United States Patent [19]

Leeke et al.

[11] Patent Number: 4,496,461
[45] Date of Patent: Jan. 29, 1985

[54] CHROMATOGRAPHY COLUMN

[75] Inventors: Gordon Leeke, Glastonbury; Chaokang Chu, E. Hartford; Nils L. Dailey, Wallingford, all of Conn.

[73] Assignee: AMF Incorporated, White Plains, N.Y.

[21] Appl. No.: 505,532

[22] Filed: Jun. 17, 1983

[51] Int. Cl.³ .............................................. B01D 15/08
[52] U.S. Cl. ............................... 210/198.2; 162/181.6; 210/502
[58] Field of Search ............ 210/635, 656, 657, 198.2, 210/502, 497.1; 55/67, 197, 386; 162/181.6

[56] References Cited

U.S. PATENT DOCUMENTS

| | | | |
|---|---|---|---|
| 3,856,681 | 12/1974 | Huber | 210/198.2 |
| 4,305,782 | 12/1981 | Ostreicher | 162/181.6 |
| 4,309,247 | 1/1982 | Hou et al. | 162/181.6 |
| 4,384,957 | 5/1983 | Crowder et al. | 210/656 |

Primary Examiner—John Adee
Attorney, Agent, or Firm—David E. Dougherty; Michael E. Zall

[57] ABSTRACT

A chromatography column for effecting chromatographic separation of at least two components of a sample flowing through the column. The column comprises a housing and at least one solid stationary phase within the housing. The stationary phase has chromatographic functionality and is effective for chromatographic separation. Means are provided for radially distributing the sample through the stationary phase and for collecting the sample after the sample has flowed through the stationary phase. The stationary phase comprises:

(a) a swellable fibrous matrix in sheet form having chromatographic functionality and being effective for chromatographic separation, spirally wound around the longitudinal axis of the solid stationary phase to form a plurality of layers around the axis; and (b) a spacer means between each layer for permitting controlled swelling thereof and enhancing the distribution of sample flowing radially through the stationary phase.

The solid stationary phase may be fabricated into a disposable cartridge for placement in the housing. A plurality of cartridges may be used either in series or parallel flow configuration in a single housing.

20 Claims, 3 Drawing Figures

CHROMATOGRAPHY COLUMN

BACKGROUND OF THE INVENTION

1. Field of the Invention

This invention relates to a novel molecular separation column, e.g. chromatography column, and more particularly to a novel column using a solid stationary phase in cartridge format.

2. Prior Art

Chromatography is a general term applied to a wide variety of separation techniques based upon the sample interchange between a moving phase, which can be a gas or liquid, and a solid stationary phase. When gas is the moving phase (or "mobile phase" as referred to in chromatographic terminology), the technique is termed gas chromatography and when liquid is the mobile phase, the technique is termed liquid chromatography.

Separations can be classified into either analytical or preparative depending on the objective. In analytical separations, the objective is high resolution separation, identification and quantification of the various components of a sample mixture. In preparative chromatography, on the other hand, the objective is the isolation of pure quantities of the desired constituents in the sample.

The collection of chromatographic column techniques can be classified in several ways and the most fundamental is based on naming the types of phases used. Liquid absorption chromatography is used extensively for organic and biochemical analysis. Ion exchange chromatography is a special field of liquid-solid chromatography and is specifically applicable to ionic species. Affinity chromatography is based on the attraction (affinity) of a ligand bonded to the solid stationary phase for a given component of the sample. Liquid-liquid or partition chromatography, involves the use of a thin layer of liquid held in place on the surface of a porous inert solid as the stationary phase.

In the chromatographic process, it is customary to pass a mixture of the components to be resolved in a carrier fluid through a chromatographic apparatus or a separative zone. The separative or resolving zone, i.e. the stationary phase, generally consists of a material referred to as a chromatographic media, which has an active chromatographic sorptive function for separating or isolating the components in the carrier fluid. The separative zone usually takes the form of a column through which the carrier fluid passes.

A major problem in the art of column chromatography is to obtain uniform fluid flow across the column. It has been recognized that the solution to this problem resides in an ability to obtain uniform packing, distribution and density of the chromatographic media within a column. To a large degree the packing problem is surmounted in the laboratory chromatography columns by using columns having a small internal diameter, generally on the order of ⅛ inch to 1½ inches. In such columns uneven chromatographic fluid flow resulting from nonuniform packing of the chromatographic media is quickly relaxed across the column diameter and does not signficantly effect analytical results.

To provide an economically feasible preparative chromatography column, the column diameter must be larger than one inch and preferably on the order of one foot or more. Attempts to scale analytical chromatography columns to a size feasible for preparative and/or production chromatography have met with substantial losses in column efficiency. It has been found that as the column diameter or cross-sectional area is increased, the separation or resolving power of the chromatography column decreases. The resolution losses can be attributed primarily to a lack of effective fluid flow distribution in the column.

Various internal column devices have been proposed to overcome the difficulties of producing large diameter preparative and production chromatography columns. Other approaches have been to provide homogenous distribution of chromatographic media and maintenance of uniform media density across the column or to develop novel type media and/or packing.

Of recent date the Assignee herein has developed unique chromatographic media, comprising in its physical form a homogeneous fibrous matrix, preferably in sheet form. Such chromatographic media are described in the following U.S. patents and patent applications:

U.S. Pat. No. 4,384,957 to Crowder, III et al;

U.S. Ser. No. 276,982, filed June 24, 1981, entitled "Process For Preparing Zero Standard Serum" to Hou;

U.S. Ser. No. 347,360, filed Feb. 9, 1982, entitled "Fibrous Media Containing Millimicron Sized Particles" to Hou;

U.S. Ser. No. 388,989, filed June 16, 1982; entitled "Process for Preparing a Zero Standard Serum" to Hou et al;

U.S. Ser. No. 401,361 filed July 23, 1982 entitled "Fibrous Media Containing Millimicron Sized Particles" to Hou; and U.S. Ser. No. 466,114, filed Feb. 14, 1983 entitled "Modified Polysaccharide Supports" to Hou.

The entire disclosures of all of these references are incorporated herein by reference.

Crowder, III et al describes a chromatography column having a substantially homogeneous stationary phase which comprises a porous matrix of fiber having particulate immobilized therein. At least one of the fiber or particulate is effective for chromatographic separations. Preferably, the stationary phase comprises a plurality of sheets in disc form stacked inside a column. The edges of the discs cooperate with the interior wall of the column to form a substantially fluid tight seal therewith, thus preventing any appreciable skewing or by-pass of fluid around the edges of the elements. In its preferred form the fluid tight seal is produced by the hydrophilic swelling of the stationary phase.

Hou (Ser. Nos. 276,982 and 388,989) describes a method for removing thyroid or steroid hormones from a serum by using a composite sheet, comprising a matrix of self bonding fibers having dispersed therein carbon particles. The sheets are used preferably in the chromatographic column described in Crowder III, et al and are also hydrophilic swellable discs or pads.

Hou (Ser. Nos. 347,360 and 401,361) describes a self supporting fibrous matrix having immobilized therein at least about 5% by weight of micro particulate, (average diameter less than 1 micron), preferably fumed silica or alumina. The media is also preferably used in the chromatographic columns disclosed in Crowder, III et al and the solid stationary phase is also hydrophilic swellable.

Hou (Ser. No. 466,114) describes a modified polysaccharide material which comprises a polysaccharide covalently bonded to a synthetic polymer. The synthetic polymer is made from a polymerizable compound which is capable of being covalently coupled directly or indirectly to the polysaccharide and one or more polymerizable compounds. The polymerizable compound contains an ionizable chemical group, a chemical group capable of transformation to an ionizable chemical group or a chemical group capable of causing the covalent coupling of the compound to an affinity ligand or biologically active molecule. The media is capable of acting as a chromatographic support for ion exchange chromatography, for affinity chromatography or as reagents for biochemical reactors. Preferably sheets of this material are loaded into an appropriately sized cylindrical column to form the desired stationary phase in a manner similar to Crowder, III et al. The preferred solid stationary phase is also hydrophilic swellable.

All of these media in their preferred embodiment, are fibrous matrices which are hydrophilic swellable, i.e. they tend to swell upon contact with aqueous systems. In a stacked disc type chromatographic column such swelling is useful in assisting producing a fluid tight seal with the interior wall of the column to form a water swellable fit therewith. Such a seal prevents skewing or bypass of the fluid around the edges of the elements.

In Hou (Ser. No. 466,114) it is indicated that the media could be used in a "jelly roll" type column, i.e. a sheet of media spirally wound around a foraminous core to form a cylinder having a plurality of layers around the axis thereof. It was subsequently found that the radial flow of a sample through such a "jelly roll" type solid phase was not evenly distributed, and there was substantial bypass of the fluid around certain areas of the media. It is believed that this is due to the swelling and resulting compression of the chromotographic media upon contact with the fluid flowing therethrough thus producing an irregular homogeneity in the solid stationary phase leading to an irregular hydrodynamic profile through the column and consequently to the establishment of preferential hydrodynamic routes which rapidly diminish the efficacy and selectivity of the chromatographic column.

Of additional relevance to this invention are the following references:

Wang et al, Biotechnology and Bioengineering XV, pages 93 (1973), describes the preparation of a "Bio-Catalytic Module" wherein collagen-enzyme membranes are layered on a supporting material, such as cellulose acetate membrane, and coiled around a central rod. Glass rods are used as spacers, which are so arranged that the distance between them is small enough to prevent the adjacent layers from contacting each other. After coiling the complex membrane upon the spacers the cartridge is then fitted into a plastic shell to form a flowthrough reactor configuration. The flow through the column is axial, i.e. the sample flowing through the column contacts the membrane in a cross-flow manner.

Wang et al (page 583) also recognizes that the flow of sample through such a device is mainly parallel to the membrane surface and that some of the enzyme molecules located within the matrix may not be readily accessible. In order to improve the contact efficiency Wang et al suggests that the sample flow through the permeable membrane under hydraulic driving pressure. In this configuration of the reactor a filter fabric serves as a backing material which separates successive layers of invertase-collagen membrane, thus preventing overlapping of the membrane layers. A perforated stainless steel tube is used as a central core element which is also used for feeding the sample. A uniform radial distribution of the substrate is achieved by metering flow through a number of holes drilled ninety degrees (90°) apart radially along the stainless tube. A spiral reactor configuration is formed by coiling alternate layers of the membrane and backing around the steel tube. The spiral cartridge is fitted into a plexiglass outer shell. The plastic housing is affixed to two threaded aluminum end plates. The sample is fed from the central tube while the reaction product is collected through a central port located on the periphery of the reactor shell.

U.S. Pat. No. 3,664,095 to Asker describes a packing material which may be spirally wound around a central axis and used for fluid treatment such as drying, heat exchange, ion exchange, molecular sieve separations and the like. Flow is axially through the apparatus, i.e. parallel to the surface of the packing material.

U.S. Pat. No. 3,855,681 to Huber describes a preparative and production chromatography column which includes a relatively inert inner core onto which is wound in a spiral pattern a relatively inert sheet of material, such as a synthetic polymeric film. Prior to winding, the film is coated with a chromatographic media. A thickness dimension of the chromatographic media is arranged substantially perpendicular to the primary direction of fluid flow through the column, i.e. flow is axial thereof and thus parallel to the surfaces of the chromatographic media.

U.S. Pat. No. 4,242,4612 Bartoli et al describes a reactor for effecting enzymic reactions in which the flow of the solution to be treated through the catalytic bed takes place radially. It is preferred to have the catalytic bed in the form of coils of enzyme-occluding fibers. The catalytic bed is formed by winding fibers on which the enzymes are supported, so as to form coils with filaments or groups of filaments arranged helically. The fibers inserted in the reactor, can also support, instead of enzymes, chelation agents, antibodies, or similar products which are immobilized, like the enzymes, by physical bonds, ion exchange, absorption, or occlusion in the filamentry polymeric structures.

U.S. Pat. No. 4,259,186 to Boeing et al (1981) describes an elongated gel filtration column having an outer wall and at least one gel chamber defined therein and adapted to be filled with a filter gel. The gel chamber is sub-divided by a plurality of interior partition walls arranged parallel to the column wall. The partition walls are of a length shorter than the length of the gel chamber.

U.S. Pat. No. 4,299,702 to Bairingi et al (1981) describes a liquid separation apparatus of the spiral type employing semi-permeable membrane sheets, between which a spacing layer is located, and utilizing the principal of reverse osmosis or ultrafiltering for separating a desired liquid component, i.e. a solvent or a solute, from a pressurized feed solution. In this type of apparatus the feed flows substantially spirally through the apparatus, i.e. parallel to the membrane. See also U.S. Pat. No. 4,301,013 to Setti et al (1981).

None of these references describe the problems associated with the use of a swellable fibrous matrix chromatographic media in sheet form utilized in a "jelly roll" type column nor the solution to such problems.

OBJECTS AND SUMMARY OF THE INVENTION

It is an object of this invention, to provide an efficient large diameter, preparative or production chromatography column using a solid stationary phase which is in cartridge form.

Another object of this invention to provide a solid stationary phase of a chromatography column which can be made in cartridge form.

A further object of this invention to provide a chromatography column which has a solid stationary phase which provides even distribution of a sample flowing radially through the stationary phase.

Still a further object of this invention to provide a chromatographic column which accommodates a swellable fibrous matrix in sheet form as the solid stationary phase.

Another object of this invention to provide a chromatography column which has a reduced pressure drop, enhanced flow and enhanced absorptive capacity.

A further object of this invention is to provide a chromatography column having essentially no determined diametric size limitation, which can be quickly and relatively inexpensively manufactured.

A still further object of this invention is to provide a chromatography column which resolves the uneven fluid flow problems encountered when attempting to scale up analytical columns to preparative and production columns.

Yet another object of the present invention to provide a solid stationary phase for liquid chromatography which insures that substantially all of the chromatographic media is utilized.

A further object of the invention is to provide an inexpensive, high quality chromatographic column which can be a disposable item in many, perhaps most, commercial processing situations.

The foregoing objects of this invention are accomplished by a chromatography column for effecting chromatographic separation of at least two components of a sample flowing through the column. The column comprises a housing and at least one solid stationary phase within the housing. The stationary phase has chromatographic functionality and is effective for chromatographic separation. Means are provided for radially distributing the sample through the stationary phase and for collecting the sample after the sample has flowed through the stationary phase. The stationary phase comprises:

(a) a swellable fibrous matrix in sheet form having chromatographic functionality and being effective for chromatographic separation, spirally wound around the longitudinal axis of the solid stationary phase to form a plurality of layers around the axis; and (b) a spacer means between each layer for permitting controlled swelling thereof and enhancing the distribution of sample flowing radially through the stationary phase.

The solid stationary phase may be fabricated into a cartridge form for placement in the housing. A plurality of cartridges may be used either in series or parallel flow configuration in a single housing.

BRIEF DESCRIPTION OF THE DRAWING

Further, characteristics features and advantages of the invention, as well as other objects and usefulness will become readily apparent to those skilled in the art from consideration of the invention as described herein and illustrated by the following drawings.

DETAILED DESCRIPTION OF THE INVENTION

The solid stationary phase utilized in this invention comprises a swellable fibrous matrix in sheet form. Preferably, this sheet is homogenous or substantially homogenous, which in effect means that the stationary phase is of a uniform or substantially uniform structure and/or composition transverse or axial to the radially flowing sample.

Figure 1:
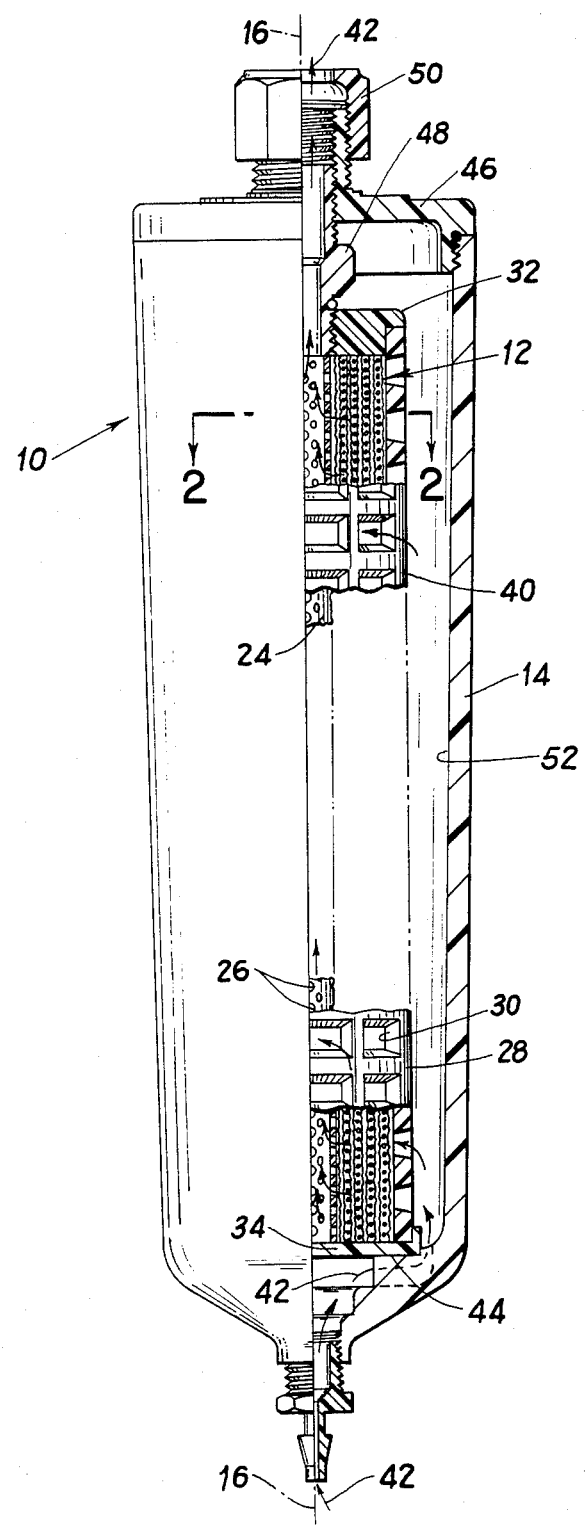
FIG. 1. is a partial sectional view of a side elevation of a preferred embodiment of the chromatography column of this invention.
Figure 2:
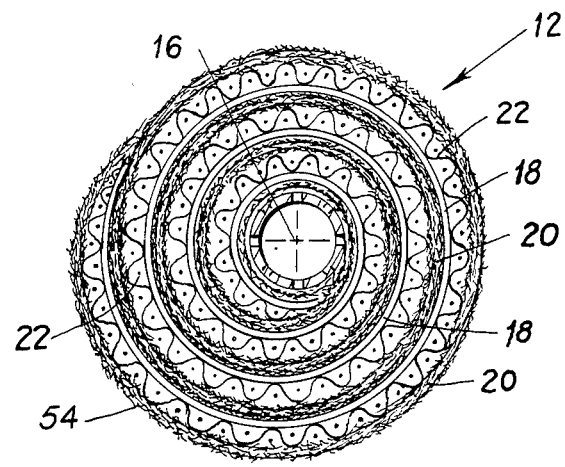
FIG. 2. is an enlarged cross-sectional view taken along line 2—2 of FIG. 1.
Figure 3:
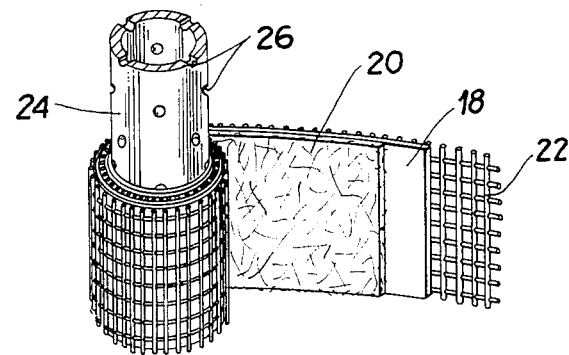
FIG. 3. is a perspective view of a portion of the solid stationary phase broken away therefrom showing the spirally wound chromatographic media and spacer means therebetween.

Referring to the drawings, wherein like character references indicate like parts, FIGS. 1 through 3 depict a preferred embodiment of the chromatography column of this invention. Referring to FIG. 1, the column, generally designated 10, is comprised of a cylindrical stationary phase 12, preferably in cartridge form, and a cylindrical chamber 14 which acts as a housing for the stationary phase 12. The solid stationary phase 12 can be inserted into a glass, metal or polymeric tube or cylinder chamber 14 having a diameter somewhat larger than the external diameter of the stationary phase 12. Suitable fluid admission, collection and monitoring systems can also be employed with the column as in conventional analytical and preparative columns. The stationary phase 12 is positioned within the chamber 14 and preferably has a longitudinal axis 16 co-axial with the axis of the cylindrical chamber 14. Optionally, a plurality of cartridges 12 may be placed in a single housing in various configurations to effect parallel and/or series flow between the cartridges (not shown). The solid stationary phase has chromatographic functionality and is effective for chromatographic separation. Referring to FIGS. 2 and 3, the stationary phase 12 is constructed of a swellable fibrous matrix, usually hydrophilic swellable, in sheet form 18 which is the active media for chromatographic separation. The chromatographic media in sheet form 18 is sandwiched between a scrim layer 20 of porous wettable fabric type material of, for example, polyester woven netting, and a nonwoven mesh 22. The composite sheet of chromatography media 18, layer of scrim 20 and mesh 22, preferably non-woven, is spirally wound around a foraminous cylindrical core 24 having a longitudinal axis 16, to form a plurality of layers around the axis 16. The mesh 22, due to the openess and thickness thereof, acts as a spacer means between each layer of media 18 which permits the controlled expansion of the swellable media 18 without closing off the porous structure of the media and enhances the distribution of the sample flowing through the stationary phase 12. The cylindrical core 24 is provided with apertures 26 for the flow of sample into the open interior of the core 24.

Referring to FIG. 1, the wound composite sheet, 18, 20 and 22 and core 24 are then slipped into an outer cylindrical member 28 which is also provided with apertures 30. The ends of the cylinders are then capped by end caps 32 and 34. The end caps 32 and 34 are sealed by thermo-plastic fusion to the outer cylindrical member 28 and also to the ends of the composite 18, 20 and 22. The fluid or sample 42 can thus flow radially from the outside to the interior of the solid stationary phase, i.e. the open interior of core 24, since the interior and exterior are completely separated by the solid stationary phase and sealed off by end caps 32 and 34.

The preformed end caps 32 and 34 are preferably applied to the cylindrical solid stationary phase 12 by heating an inside face of the thermo-plastic end cap to a temperature sufficient to soften and preferably not liquify, a sufficient amount of the end cap to form a thermo-plastic seal with the end of the cylinder 28. All of the edges of one end of the cylinder 28 are then embedded into the softened material. The softened material is then hardened, typically by ambient conditions, to form a thermo-plastic sealing relationship between the sealing surface of the end caps 32 and 34, the cylinder 28 and the ends of the solid stationary phase 12 to form a leak-proof seal. Such methods of applying end caps are well known in the filtration art, see for example, U.S. Ser. No. 383,383 and U.S. Ser. No. 383,377 filed on May 28, 1982 to Meyering et al and Miller, respectively. Optionally, the endcaps can be molded integrally in-situ onto the solid stationary phase.

End caps of thermo-plastic materials are preferred because of the ease of bonding, but it is also possible to use thermo-setting resins in a thermo-plastic, fusible or heat softenable stage of polymerization, until the bondings have been effected, after which the curing of the resin can be completed to produce a structure which can no longer be separated. Such a structure is autoclavable without danger of destroying the fluid tight seal between the cylinder 28, the solid stationary phase 12 and the end caps 32 and 34. Thermo-plastic resins whose softening point is sufficiently high so that they are not softened under sterilizing auto-claving conditions are preferred for biomedical use. Exemplary of the plastic materials which can be used are polyolefins.

Referring to FIG. 1 the preferred cartridge 40 has an end cap 34 on one end which does not open to the exterior of outer cylindrical member 28 but is closed off. This end cap 34 can nest on the bottom end wall 44 of cylindrical housing 14 while still permitting the flow of sample 42 into the chamber 14 around the outside of outer cylindrical chamber 28, or this lower end cap 34 of cartridge 40 is in spaced apart relationship from the bottom end wall 44 of cylindrical chamber 14, thus permitting the flow of sample 42 into the chamber 14.

The upper end of cartridge 40 has an end cap 32 which is in fluid communication with cylindrical core 24 thus permitting the flow of fluid from the center of cylindrical core 24 to the outside of end cap 32. A fitting 48, is inserted into end cap 32 so that it may engage the end wall 46 of cylindrical chamber 14. This fitting may be threaded (as shown) or separately or integrally molded with the endcap and having o-ring seals thereon. End wall 46 has thereon a threaded nipple 50 which permits the flow of treated sample 42 to pass from the core 24 through end cap 32, and end wall 46 into the process stream for additional processing. The end wall 46, and optionally end wall 44 may be threadedly attached to the wall 52 of cylindrical chamber 14 for easy access to the interior for cleaning and insertion of the cartridge 40.

The present invention as conceived utilizes known media and known media preparation techniques, specifically those described in the aforementioned co-pending applications and patents. This preferred media is fibrous, in sheet form and generally has the characteristics that it is hydrophilic swellable. The preferred chromatographic media is that described in the aforementioned Crowder, III et al patent, and Hou applications, the entire disclosures of which are incorporated herein by reference. It should be realized however that this invention is applicable to any type of swellable media in sheet form, whether it is hydrophilic swellable or otherwise.

In order to provide a chromatographic media matrix which is coherent and handleable, it is desirable that at least one of the components which go into forming the porous matrix be a long, self bonding structural fiber. Such fiber gives the stationary phase sufficient structural integrity in both the wet "as formed" condition and in the final dry condition. Such a structure permits handling of the phase, in particular a sheet, during processing and at the time of its intended use. Preferably the sheets which form the chromatograhic media are formed by vaccum felting an aqueous slurry of fibers. The sheets may also be pressure felted or felted from a non-aqueous slurry. The sheet shows a uniform high porosity, with excellent flow characteristics and is substantially homogeneous. In general, the media can range in thicknesses of from about 5 mils to about 30 mils (dry), however thicker or even thinner media may be utilized provided the sheet can be spirally wound to produce a cartridge which can perform as described herein. The media can swell to at least 25% this thickness, and generally greater, e.g. two to four times this thickness.

It is important when constructing the chromatography column of this invention that the chomatographic media used in the column be of uniform thickness throughout its length and width and that the media have a substantially uniform density throughout. It is preferred that the layer of media be substantially homogenous with respect to itself, however, for certain applications and material it is to be understood that non-homogenous construction may be employed.

Since the solid stationary phase is intended in use to effect separation by maintaining a substantial pressure differential across the solid stationary phase, it is essential that the solid stationary phase have a sufficient degree of compressive strength to withstand deformation under such loads as may be imposed upon it. Such compressive strength must not only exist in the media itself but in the spacer means and the internal core upon which the chromatography media, or solid stationary phase is compressed.

Due to the swellability of the media, a key element of this invention is the spacer means between each layer of the media. The spacer means permits controlled expansion of the media and enhancement of the distribution of sample flowing through the stationary phase. The spacer means located between each layer of the swellable chromatographic media provides for the axial and the circumferential movement of the sample as the sample passes radially through the solid stationary phase. The spacer means functions to uniformly control thickness and density of the chromatographic media during use. In addition, the spacer means can serve as a backing or support for the layer of chromatographic media. This latter aspect is particularly useful during the manufacturing phase.

It is prefered that the spacer means be composed of a material which is inert with respect to the chromatographic process. By inert it is meant the material does not adversly effect the function of the solid stationary phase.

Referring to FIGS. 2 and 3, the spacer means may comprise two elements thereof, i.e. the scrim 20 and the mesh 22. The scrim material 20 functions to channel, to a certain extent, the sample flowing through the media and substantially evenly disperse the sample axially and circumferentially across the media. The mesh material provides spacing between the media to permit controlled expansion thereof to prevent the "cut-off" of flow therethrough by compression of the permable media and also assists in distributing or channelling the sample flowing radially through the media both axially and circumferentially.

The scrim 20 is preferably a porous material which is wettable by the sample to maximize the distribution of sample during flow through the stationary phase. Such wettable scrims can, for example, be made of non-woven textiles and cloth, papers and similar materials. Suitable wettable scrims include polyester non-woven fibrous webs or woven webs, using mono-filaments or multi-filament yarn, the mono-filaments being preferred in terms of open structure and lower pressure drops, polyamide fiber woven webs, woven and non-woven webs of aromatic polyamides, and other relatively fibrous products such as cellulose, regenerated cellulose, cellulose esters, cellulose esters, glass fiber, and similar materials. Cellulosic and synthetic fiber filter papers may also be used as the scrim matrial as well as perforated plastic sheets and open mesh expanded plastics. These latter more open type scrims merge, to a certain extent, into the mesh spacer material in function. It is conceivable that the function of the scrim and mesh may be combined into one type material of proper wettability and pore structure to function in distributing the sample flowing through the stationary phase both axially and circumferentially while still permitting controlled expansion of the media to allow the passage of the sample therethrough to the next layer of media, for example, a porous compressible spongelike material.

More specifically preferred scrims are polyester spun bonded non-woven webs trademarked REEMAY from DuPont. Eaton Dikemann Corps, HOLLYTEX; polypropylene webs such as HOLLYTEX; Kendall Corps NOVONETTE Crown Zellerbach's" 0.75 oz/sq. yd.; and Kendall's WEBRIL; Lutravil Sales Co's. LUTRASIL and Chicopee Mills' VISKON may also be used.

The mesh material is a more open type of material having openings ranging, for general guidance, from 1/16 inch to a ½ inch and is at least equivalent in thickness to the thickness of the media.

It should be noted that the thickness of the spacer means, i.e. the scrim and particularly the mesh material, and the pore size of each to be used may be readily determined by one skilled in the art by performing tests which vary these factors. Such factors as the openness and thickness of these spacer means are highly dependent on the type of media utilized, e.g. swellability, wettability, thickness, chemical composition, etc., the flow rate of the sample through the stationary phase, the surface area of the stationary phase, e.g. number of windings, thickness of media, diameter of stationary phase, etc. It is thus very difficult to clearly specify these variables, other than to say that these may be determined by either trial and error or more elaborate testing procedures to determine the optimum parameters. For general guidance, it has been found that a scrim material having a thickness of from about 5 MILS to about 10 mils and mesh having a thickness of from about 5 mils to about 30 mils and openings of about 1/16 to about ¼ inch is suitable.

The preferred scrim material, at this time, is polyester Reemay Grade 2014.

The preferred mesh material, at this time, is polypropylene CONWED (GRADE TD-620).

Referring to FIG. 2, after winding the chromatography media 18 on the core 24, the exterior surface 54 thereof is completely wrapped with the scrim material 20.

The overall width of the stationary phase in accordance with the present invention can be infinite, the actual diameter being limited only by practical considerations such as space requirements. Since the diameter or width of the overall column can be increased without theoretical limitation, the sample size or amount of substance to be separated in the bed is not limited. Thus the diameter can be increased to separate the desired amount of sample substance to be produced.

In operation, the sample is driven radially through the stationary phase and separated into distinct chromatographic fractions by the chromatographic media. The spacer means induces and permits circumferential and axial flow of this stream as it moves through the column and therefore provides for improved resolution and utilization of the medias potential capacity.

Referring to FIG. 1, the sample is preferably introduced at the bottom of the column flowing to the outer surface of the solid stationary phase and then flowing radially inwardly through the layers of chromatographic media and spacer means into the perforated central tube 24 and is withdrawn centrally. It is apparent, from what has been set forth above that the radial flow can also be caused to circulate in the opposite direction.

The chromatographic columns of this invention may be used for any of the well-known chromatographic separations usually performed with conventional columns. Additionally, the columns of the present invention may be found useful in the areas where conventional columns are impractical.

The novel columns of this invention can be used for separations in the analytical and preparative fields. The columns can be connected to all common types of chromatographic equipment. Several columns or cartridges of solid stationary phase can be connected in series or parallel. In large units, the columns can contain identical or different chromatographic media and can be of identical or different length and/or diameter.

It has been found that the aforedescribed cartridge 40 when used in conjunction with housing 14 produces unexpected results in that the flow of sample through the column is enhanced without destroying the absorptive capacity of the media. Additionally when protein and dye staining tests were performed it was found that the solid stationary phase of this invention provided even distribution of sample flow therethrough without an increase in pressure drop when compared to a spirally wound cartridge not utilizing the spacer means described herein.

From the foregoing it can be seen that a convenient cartridge configuration has been invented which is easy to install, operate, and disassemble and is easily adaptable to any batch size or continuous type operation by the use of multiple configurations. Additionally the chromatography column cartridge has excellent structural integrity.

The cartridges decrease total processing time and when used with the proper chromatographic media has excellent binding capacity. The cartridges may be used with standard type pumps or gravity feed and utilized, in their preferred mode, at from 5 to 50 PSI. The cartridges of chromatographic media are totally enclosed and completely self contained to ensure sterile conditions. Due to the fact that the solid stationary phase cartridge is manufactured in a factory and assembled therein each cartridge is virtually identical to the other, does not vary as in previously known columns and eliminates the dependence upon packing expertise. Additionally there is no premeasuring of chromatographic media, no media loss due to handling, no packing problems, no fines generation and removal within the column and other problems associated with packing chromatographic cartridges. The column is simple to operate, does not produce any channeling by passing or shifts in bed volume. The chromatographic cartridges allow scale up from milligram laboratory quantities to megagram production quantities. The cartridge provides rigidity and strength and are particularly useful as a high flow medium pressure matrix and is highly suitable for large scale protein or non-protein purifications.

The present invention has been described in relation to several embodiments. Upon reading the specification one of ordinary skill in the art would be able to effect various alterations or, changes in or substitutions of equivalence to the present invention as disclosed. It is intended that the invention as conceived be limited only by the definition of the invention contained in the appended claims.

What is claimed is:

1. A chromatography column for effecting chromatographic separation of at least two components of a sample flowing radially therethrough comprising:
   a housing;
   at least one solid stationary phase in said housing having a longitudinal axis, said phase having chromatographic functionality and being effective for chromatographic separation;
   a means for radially distributing the sample through the stationary phase;
   a means for collecting the sample after the sample has radially flowed through the stationary phase;
   wherein the stationary phase comprises:
   (a) a swellable fibrous matrix in sheet form having chromatographic functionality and being effective for chromatographic separation, spirally wound around the longitudinal axis of the solid phase to form a plurality of layers around the axis;
   (b) a spacer means between each layer separating the layers for permitting controlled swelling of the matrix and enhancing the distribution of sample flowing radially through the stationary phase by channelling the sample flow through the matrix and substantially evenly dispersing the sample axially and circumferentially across the matrix.

2. The column of claim 1, wherein the housing and stationary phase are cylindrical and coaxial and the housing has a diameter greater than the stationary phase.

3. The column of claim 1, wherein the swellable matrix swells at least about 35% of its thickness.

4. The column of claim 1, wherein the swellable matrix is hydrophilic swellable.

5. The column of claim 1, wherein the matrix is spirally wound around a foraminous cylindrical core.

6. The column of claim 5, wherein the foraminous cylindrical core is in fluid communication with the means for collection.

7. The column of claim 5, wherein the stationary phase is enclosed in an outer cylindrical member having apertures therein.

8. The column of claim 7, wherein the ends of the stationary phase are capped at one end by an end cap which has an opening therein which is in fluid communication with the cylindrical core and at the other end by a solid end cap.

9. The column of claim 1 or 8, wherein the spacer means comprises:
   (a) a scrim layer for channelling the sample flow through the matrix and substantially evenly dispersing the sample axially and circumferentially across the matrix; and
   (b) a mesh layer to provide a spacing between the layers to permit controlled expansion thereof and assist in distributing the sample axially and circumferentialy across the matrix.

10. The column of claim 9, wherein the scrim layer completly covers the exterior surface of the solid stationary phase.

11. The column of claim 1 or 8 wherein the solid stationary phase is a disposable cartridge.

12. A solid stationary phase having a longitudinal axis, said phase having chromatographic functionality and being effective for chromatographic separation of at least two components of a sample flowing radially therethrough, wherein the stationary phase comprises:
   (a) a swellable fibrous matrix in sheet form having chromatographic functionality and being effective for chromatographic separation, spirally wound around the longitudinal axis of the solid phase to form a plurality of layers around the axis;
   (b) a spacer means between each layer separating the layers for permitting controlled swelling of the matrix and enhancing the distribution of sample flowing radially through the stationary phase by channelling the sample flow through the matrix and substantially evenly dispersing the sample axially and circumferentially across the matrix.

13. The stationary phase of claim 12, wherein the swellable matrix swells at least about 25% its thickness.

14. The stationary phase of claim 12, wherein the swellable matrix is hydrophilic swellable.

15. The stationary phase of claim 12, wherein the matrix is spirally wound around a foraminous cylindrical core.

16. The stationary phase of claim 15, wherein the stationary phase is enclosed in an outer cylindrical member having apertures therein.

17. The stationary phase of claim 16, wherein the ends of the stationary phase are capped at one end by an end cap which has an opening therein which is in fluid communication with the cylindrical core and at the other end by a solid end cap.

18. The stationary phase of claim 12 or 17, wherein the spacer means comprises:
   (a) a scrim layer for channelling the sample flowing through the matrix and substantially evenly dispersing the sample axially and circumferentially across the matrix; and
   (b) a mesh layer to provide a spacing between the layers to permit controlled expansion thereof and assist in distributing the sample axially and circumferentially across the matrix.

19. The stationary phase of claim 18, wherein the scrim layer completly covers the exterior surface of the solid stationary phase.

20. The stationary phase of claim 12 or 17 which is a disposable cartridge.

* * * * *